(12) United States Patent
O'Shea et al.

(10) Patent No.: US 8,273,913 B2
(45) Date of Patent: Sep. 25, 2012

(54) AMIDATION PROCESS FOR THE PREPARATION OF CATHEPSIN K INHIBITORS

(75) Inventors: Paul O'Shea, Westmount (CA); Francis Gosselin, Boulder, CO (US)

(73) Assignee: Merck Canada Inc., Quebec (CA)

( * ) Notice: Subject to any disclaimer, the term of this patent is extended or adjusted under 35 U.S.C. 154(b) by 447 days.

(21) Appl. No.: 12/593,695

(22) PCT Filed: Mar. 31, 2008

(86) PCT No.: PCT/CA2008/000605
§ 371 (c)(1),
(2), (4) Date: Sep. 29, 2009

(87) PCT Pub. No.: WO2008/119176
PCT Pub. Date: Oct. 9, 2008

(65) Prior Publication Data
US 2010/0130782 A1    May 27, 2010

Related U.S. Application Data

(60) Provisional application No. 60/921,321, filed on Apr. 2, 2007.

(51) Int. Cl.
*C07C 255/46* (2006.01)
(52) U.S. Cl. ......................... 558/434; 556/426
(58) Field of Classification Search ................... 558/426, 558/434
See application file for complete search history.

(56) References Cited

U.S. PATENT DOCUMENTS

2003/0232863 A1* 12/2003 Bayly et al. ................... 514/357

FOREIGN PATENT DOCUMENTS

| CA | 2477657 | 9/2003 |
|---|---|---|
| WO | WO03/075836 | 9/2003 |
| WO | 2005019161 A1 | 3/2005 |
| WO | 2005021487 A1 | 3/2005 |
| WO | 2006034004 A2 | 3/2006 |

OTHER PUBLICATIONS

Gauthier, JY et al., Bioorganic & Medicinal Chemistry Letters, vol. 17, 2007, pp. 4929-4933, "The identification of potent, selective, and bioavailable cathepsin S inhibitors".
Supplementary European Search Report dated (Oct. 17, 2011), for related European Application No. EP08 73 3702; 7 pages.

* cited by examiner

*Primary Examiner* — Shailendra Kumar
(74) *Attorney, Agent, or Firm* — Nicole M. Beeler; Gerard M. Devlin

(57) ABSTRACT

This invention describes an amidation process whereby amino acids of the Formulae IIA or IIB can be activated and treated with an amine in the presence of a base to yield amides of the Formula (I), without loss of optical purity.

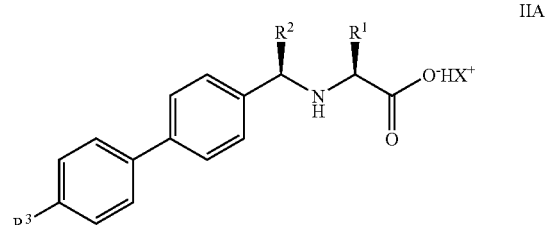

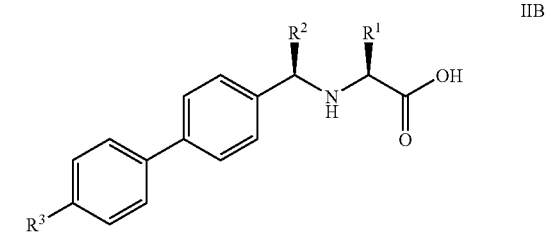

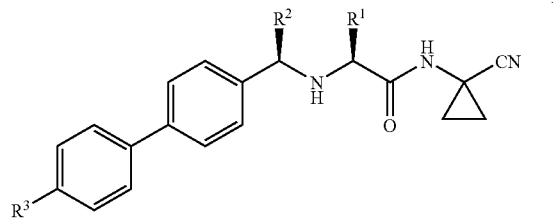

5 Claims, 3 Drawing Sheets

AMIDATION PROCESS FOR THE PREPARATION OF CATHEPSIN K INHIBITORS

CROSS REFERENCE TO RELATED APPLICATIONS

This application is a U.S. National Phase application under 35 U.S.C. §371 of PCT Application No. PCT/CA2008/000605 filed Mar. 31, 2008, which claims priority from U.S. Provisional Application Ser. No. 60/921,321, filed Apr. 2, 2007.

BACKGROUND OF THE INVENTION

This invention describes an amidation process whereby perfluorinated amino acids can be activated and treated with an amine in the presence of a base to yield amides, without loss of optical purity. The resulting amides are selective cathepsin K inhibitors which can be used in the treatment of osteoporosis and metastatic bone disease.

SUMMARY OF THE INVENTION

By this invention, there are provided processes for the preparation of compounds of structural formula I:

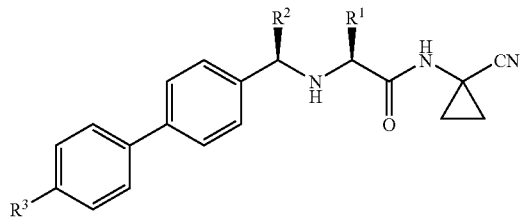

I comprising amidating a salt of formula IIA or an acid of formula IIB

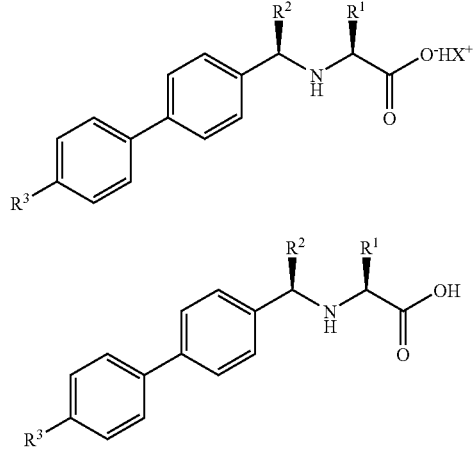

IIA

IIB with 1-aminocyclopropane carbonitrile, in the presence of a coupling agent, a base and a solvent;
wherein $R^1$ is $C_{1-6}$ alkyl or $C_{1-6}$ haloalkyl;
$R^2$ is $C_{1-6}$ alkyl or $C_{1-6}$ haloalkyl;
$R^3$ is $SO_m(C_{1-6}$ alkyl);
X is a tertiary amine, a secondary amine or a metal salt; and
m is an integer from zero to two.

DETAILED DESCRIPTION OF THE INVENTION

Figure 1:
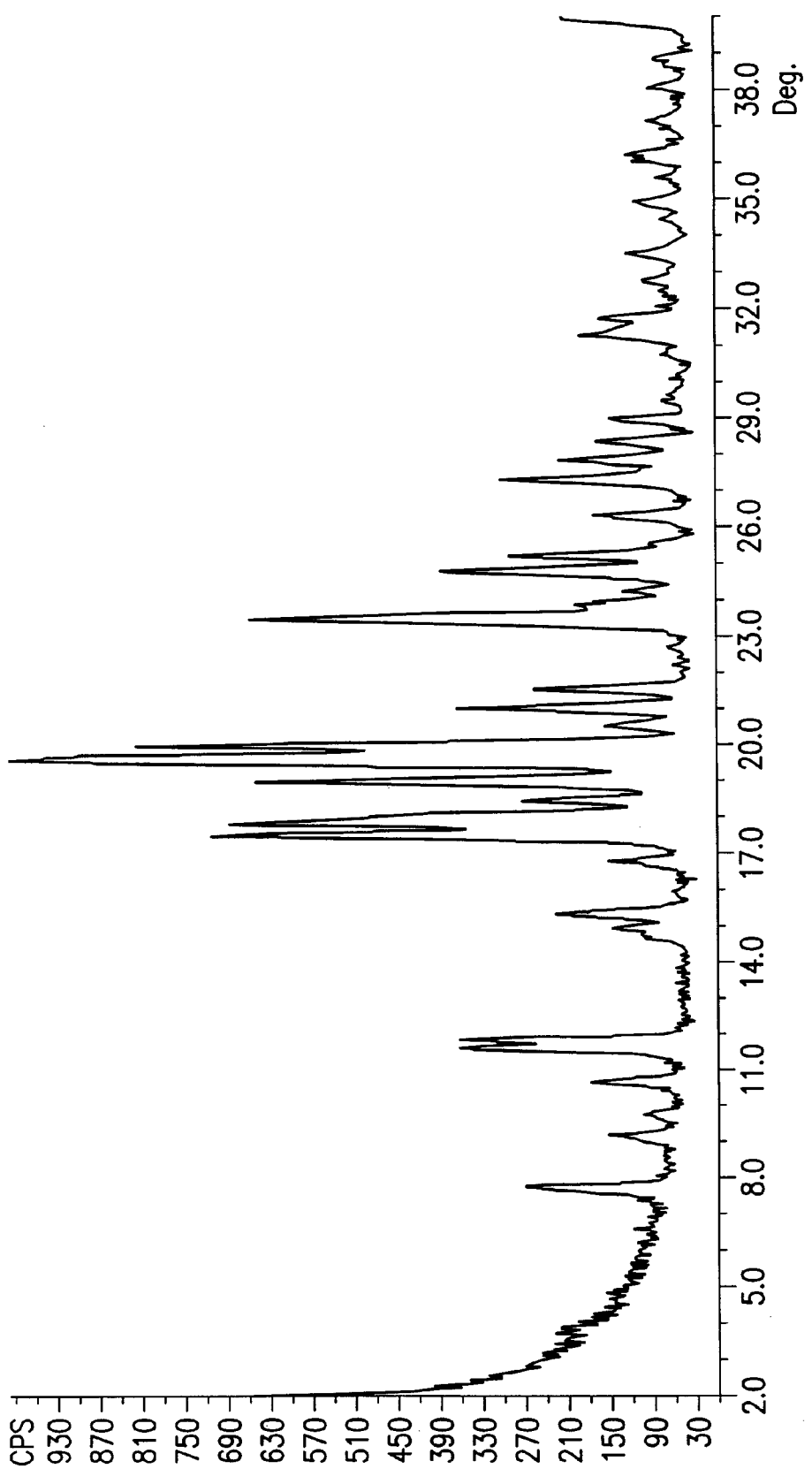
FIG. 1 is a characteristic X-ray diffraction pattern of crystalline $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide.
Figure 2:
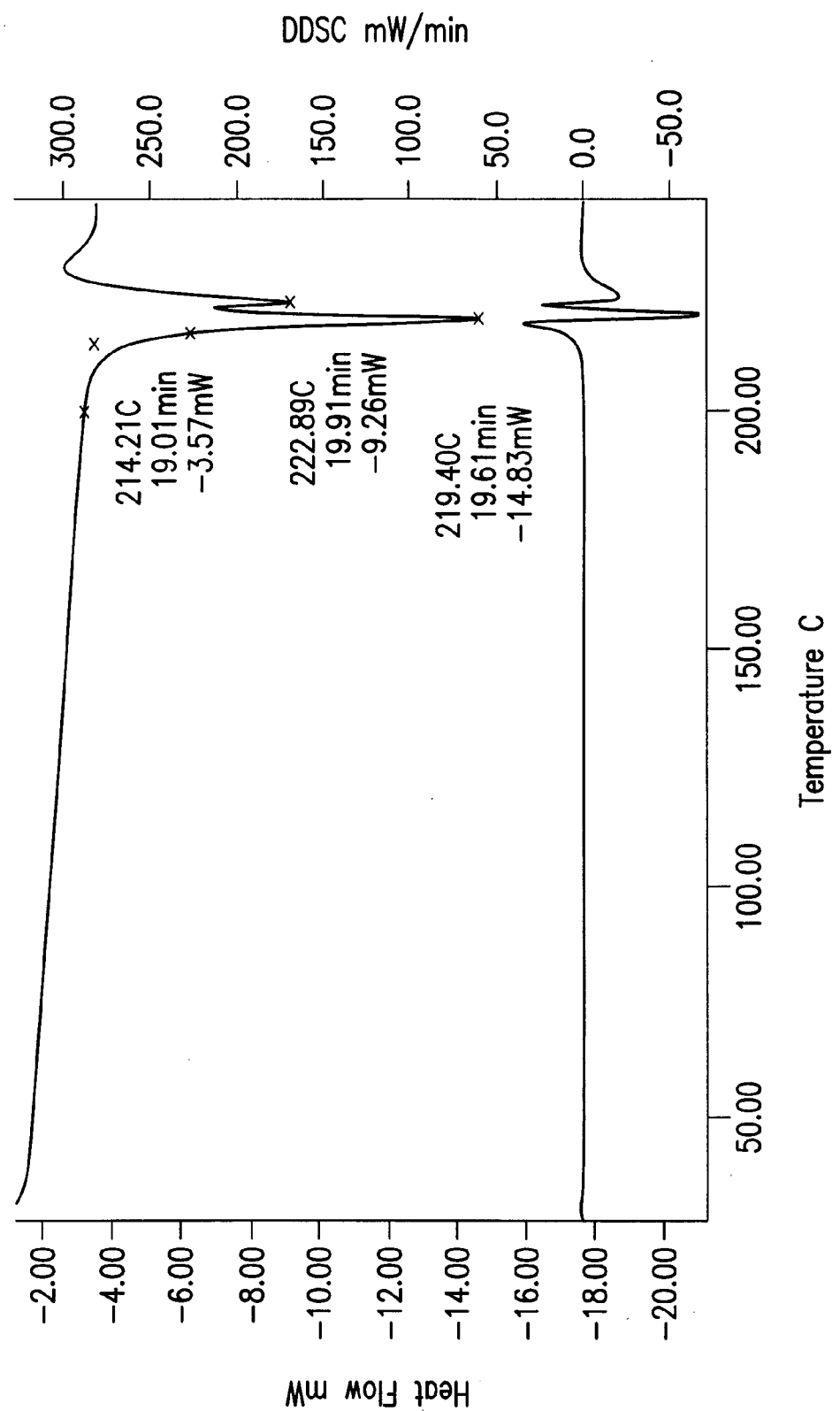
FIG. 2 is a typical differential scanning calorimetry (DSC) curve of crystalline $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide.
Figure 3:
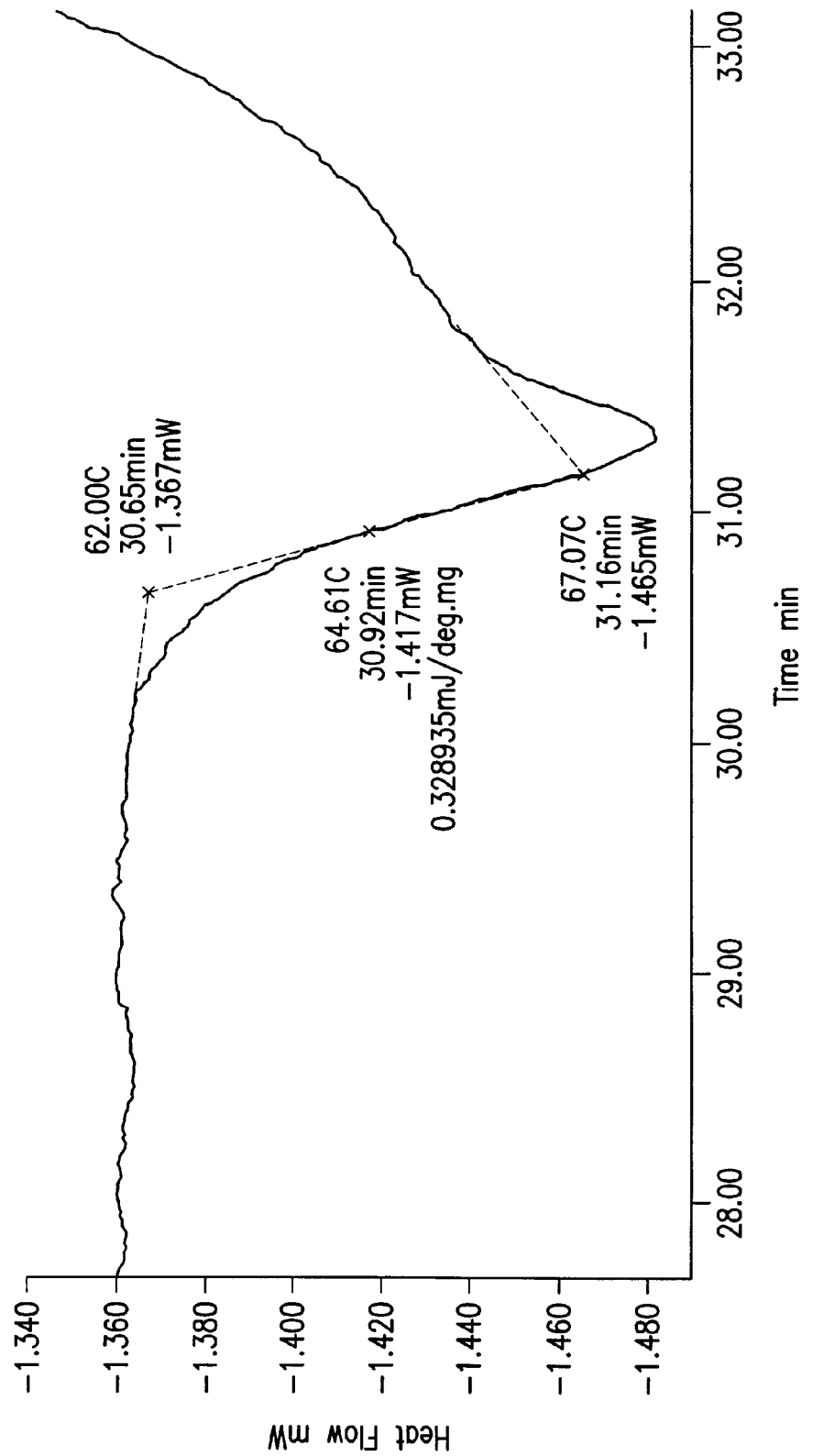
FIG. 3 is a typical differential scanning calorimetry (DSC) curve of amorphous $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide.

By this invention, there are provided processes for the preparation of compounds of structural formula I:

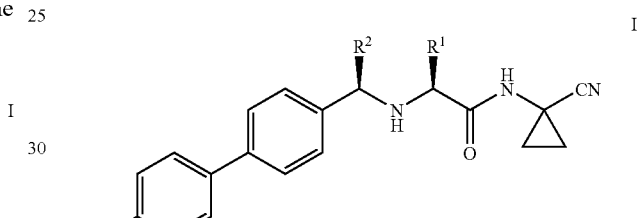

I comprising amidating a salt of formula IIA or an acid of formula IIB

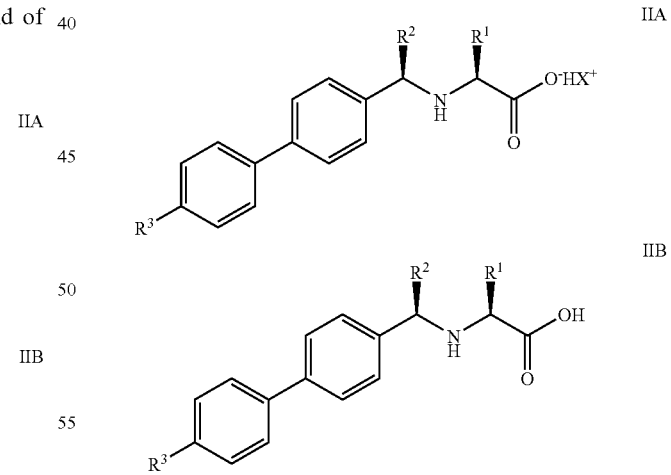

IIA

IIB with 1-aminocyclopropane carbonitrile, in the presence of a coupling agent, a base and a solvent;
wherein $R^1$ is $C_{1-6}$ alkyl or $C_{1-6}$ haloalkyl;
$R^2$ is $C_{1-6}$ alkyl or $C_{1-6}$ haloalkyl;
$R^3$ is $SO_m(C_{1-6}$ alkyl);
X is a tertiary amine, a secondary amine or a metal salt; and
m is an integer from zero to two.

In an embodiment of the invention, $R^1$ is $C_{1-6}$ haloalkyl. In a class of the invention, $R^1$ is (2-fluoro,2-methyl)propyl.

In an embodiment of the invention, $R^2$ is $C_{1-6}$ haloalkyl. In a class of the invention, $R^2$ is trifluoromethyl.

In an embodiment of the invention, $R^3$ is $SO_2(C_{1-6}$ alkyl). In a class of the invention, $R^3$ is $SO_2CH_3$.

In an embodiment of the invention X is a secondary amine. In a class of the invention, X is DCHA.

In an embodiment of the invention, the compound of formula I is

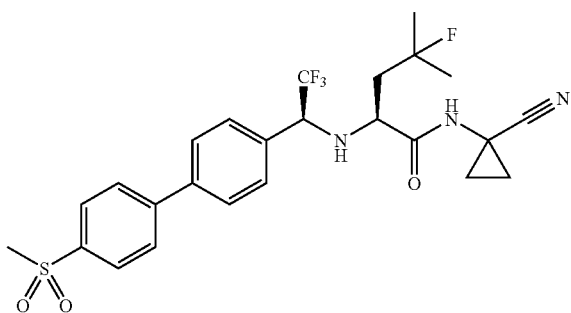

$N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide.

An α-aminoacid or its corresponding salt is activated, followed by treatment with an amine in the presence of a base. Activation may be achieved by formation of an acyl halide, mixed anhydride or by treatment with a coupling agent, with or without an additional activating agent, in the presence of a suitable base and in a suitable solvent.

In an embodiment of the invention, the coupling agent is a carbodiimide, phosphonium salt or uronium salt. In a class of the invention, the coupling agent is EDC.

In an embodiment of the invention, the activating agent is HOBt, N-hydroxy succinimide, 2-hydroxypyridine, N-hydroxyphthalimide or CDI. In a class of the invention, the activating agent is HOBt.

In an embodiment of the invention, the base is N-methyl morpholine, TEA, N-ethyldiisopropylamine, 2,6-lutidine, 2,4,6 collidine or 1-methylpiperidine. In a class of the invention, the base is N-methyl morpholine.

In an embodiment of the invention, the solvent is DMF, DMAc, NMP, acetonitrile, THF, or DMSO. In a class of the invention, the solvent is DMF.

In an embodiment of the invention is the process for the preparation of a compound of structural formula:

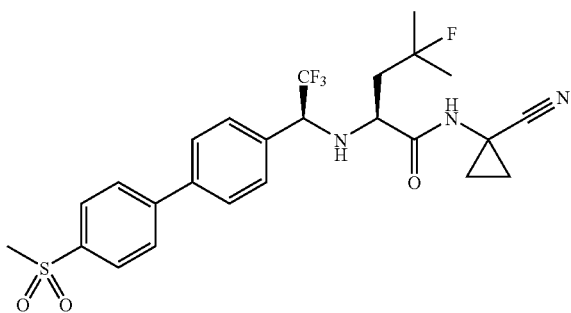

comprising amidating a salt:

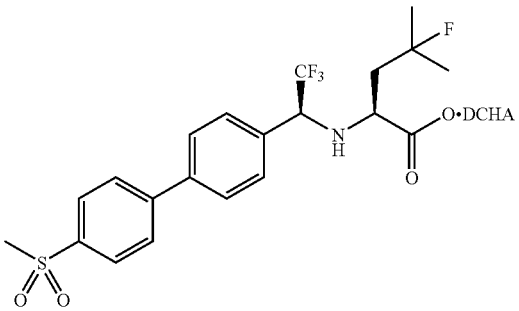

with 1-aminocyclopropane carbonitrile, in the presence of EDC, HOBt, N-methyl morpholine and DMF.

The term "alkyl" as used herein shall mean a substituting univalent group derived by conceptual removal of one hydrogen atom from a straight or branched-chain acyclic saturated hydrocarbon (i.e., —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, etc).

As appreciated by those of skill in the art, "halo" or "halogen" as used herein is intended to include chloro, fluoro, bromo and iodo. The term "keto" means carbonyl (C=O). The term "alkoxy" as used herein means an alkyl portion, where alkyl is as defined above, connected to the remainder of the molecule via an oxygen atom. Examples of alkoxy include methoxy, ethoxy and the like.

The term "haloalkyl" means an alkyl radical as defined above, unless otherwise specified, that is substituted with one to five, preferably one to three halogen. Representative examples include, but are not limited to trifluoromethyl, dichloroethyl, and the like.

The term "tertiary amine" includes, but is not limited to, trimethylamine, triethylamine, tripropylamine, dimethylethanolamine and bis-tris.

The term "secondary amine" includes, but is not limited to, dimethyl amine, diethylamine, methylethanolamine, aziridine, azetidine, pyrrolidine, piperidine, and dicyclohexylamine (DCHA).

The term "metal salt" includes, but is not limited to, salts of aluminum, antimony, calcium, copper, gold, iron, lead, lithium, magnesium, platinum, potassium, sodium, silver, strontium, tin, titanium, tungsten and zinc. Preferred metal salts include salts of lithium, sodium, potassium, magnesium, calcium, aluminum and zinc.

The term carbodiimide refers to a class of coupling agents that are often used to activate carboxylic acids towards amide formation. Nonlimiting examples or carbodiimides include: DCC (N,N'-dicyclohexylcarbodiimide), DIC (N,N'-diisopropylcarbodiimide) and EDC (1-ethyl-3-(3-dimethylaminopropyl) carbodiimide hydrochloride).

The term phosphonium salt refers to salts containing the phosphonium ion (($PH_4^+$) ion) which are useful as coupling agents. Nonlimiting examples of phosphonium salts include: phosphonium iodide, tetramethylphosphonium iodide, PyBrOP (Bromo-tris-pyrrolidino phosphoniumhexafluorophosphate) and PyAOP ((7-Azabenzotriazol-1-yloxy)tripyrrolidinophosphonium hexafluorophosphate).

The term uronium salt refers to salts containing the uronium ion. Nonlimiting examples of uronium salts include: HBTU (2-(1H-Benzotriazole-1-yl)-1,1,3,3-tetramethyluronium hexafluorophosphate), HATU (2-(7-Aza-1H-benzotriazole-1-yl)-1,1,3,3-tetramethyluronium hexafluorophosphate), TATU ((O-(7-Azabenzotriazole-1-yl)-N,N,N',N'- tetramethyluronium tetrafluoroborate) and TBTU (2-(1H-Benzotriazole-1,1,3,3-tetramethyluronium tetrafluoroborate).

Crystalline $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide is characterized by an X-ray powder diffraction (XRPD) pattern, collected using copper Kα radiation, corresponding to characteristic reflection peaks at 19.7, 20.1 and 17.6 degrees. The pattern is further characterized by characteristic reflection peaks at 23.6, 17.9 and 19.1 degrees. The pattern is further characterized by characteristic reflection peaks at 24.8, 11.7 and 11.9 degrees. The XRPD patterns are measured using a Scintag XDS-2000, Si(Li) Peltier-cooled solid state detector, CuKα source at a generator power of 45 kV and 40 mA, and divergent beam (2 mm and 4 mm) and receiving beam slits (0.5 mm and 0.2 mm). Scan range is set from 2-40° 2θ with a step size of 0.02° and a count time of 2 seconds. The sample is measured on a quartz disk with spinning to reduce potential in-plane orientation effects. Peak positions are verified weekly using a standard corundum plate (NIST SRM 1976).

In addition to the X-ray powder diffraction pattern described above, crystalline $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide is characterized by melting onset at 214° C. The DSC thermal behaviour is investigated using a Seiko robotic DSC (RDC-220). DSC analyses (n=2) are carried out in crimped aluminium pans (2, 10, and 20° C./min, 80 mL/min nitrogen). The DSC is calibrated for temperature and heat flow with gallium (Goodfellow, 99.99% Pure), indium (Goodfellow, 99.999% Pure), and tin (MST SRM 2220).

Amorphous $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide can also be observed. The glass transition temperature for the amorphous form is evaluated by temperature cycling and is measured at the mid-point. The sample are heated from −30° C. to 75° C. at 10° C./min following by cooling at 10° C./min to −30° C., and then the sample is re-heated to 180° C. at 10° C./min (n=1). A glass transition temperature ($T_g$) of about 64° C. (mid-point, 10° C./min) followed by an exothermic transition at a peak temperature of 101° C., attributed to recrystallization of amorphous material, is obtained for a predominantly amorphous sample. The DSC thermal behaviour is investigated using a Seiko robotic DSC (RDC-220). DSC analyses (n=2) are carried out in crimped aluminium pans (2, 10, and 20° C./min, 80 mL/min nitrogen). The DSC is calibrated for temperature and heat flow with gallium (Goodfellow, 99.99% Pure), indium (Goodfellow, 99.999% Pure), and tin (NIST SRM 2220).

In the schemes and examples below, various reagent symbols and abbreviations have the following meanings:

DMAc: N,N'-Dimethyl acetamide
DCHA: Dicyclohexylamine
MTBE: Methyl-t-butylether
iPAc: Isopropyl acetate
DMF: N,N'-Dimethylformamide
THF: Tetrahydrofuran
TEA: Triethylamine
DMSO: Dimethylsulfoxide
NMP: 1-Methyl-2-pyrrolidinone
CDI: N N'-Carbonyldiimidazole
HATU: O-(7-Azabenzotriazol-1-yl)-N,N,N'N'-tetramethyluronium hexafluorophosphate
EDC: 1-Ethyl-3-[3-dimethylaminopropyl]carbodiimide hydrochloride
HOBt: N-Hydroxybenzotriazole
NMM: N-methyl morphonline Scheme 1 depicts the reaction of a substituted α-amino acid or its salt with an amine in the presence of a coupling agent, an activator and a base to yield the corresponding α-amino amide product without epimerization of the α-stereocenter.

SCHEME 1

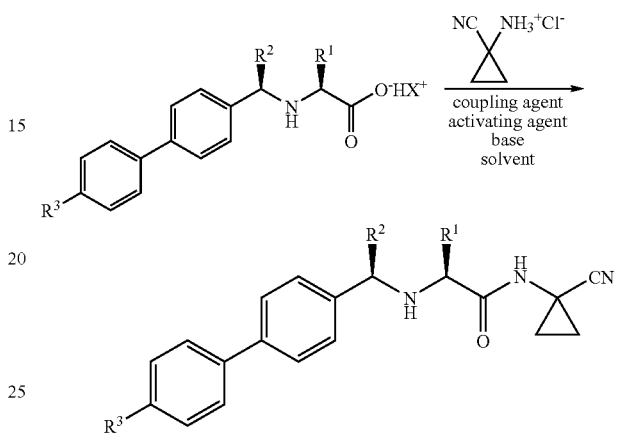

The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

Example 1

4-FLUORO-N-{(1S)-2,2,2-TRIFLUORO-1-[4'-(METHYLSULFONYL)BIPHENYL-4-YL]ETHYL}-L-LEUCINE DICYCLOHEXYLAMINE SALT

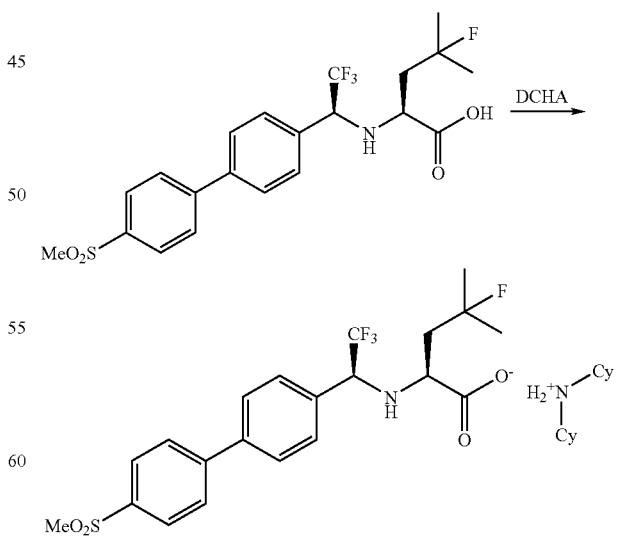

Biphenyl acid (20.74 g) was dissolved in 2-propanol (186 mL)/water (20.7 mL). A solution of N,N-dicyclohexylamine (9.82 mL) in 2-propanol (21 mL)/water (2 mL) was added (~10% of volume) and the solution was seeded with DCHA salt (10 mg). A heavy seed bed formed and the slurry was let stir at rt for 30 min. Addition of DCHA was continued over 20-30 min. The slurry was let stir at rt overnight and filtered. The filter cake was washed with 2-propanol/water (2×30 mL, 10:1) and MTBE (2×30 mL). DCHA salt was obtained as a white solid, 24.4 g, 84% yield. $^1$H NMR (CD$_3$OD) δ 8.07 (d, 2H, J=8.0), 7.94 (d, 2H, J=8.0), 7.75 (d, 2H, J=8.0), 7.61 (d, 2H, J=8.0), 4.31 (m, 1H), 3.46 (bq, 1H, J=4), 3.22 (m, 2H), 3.19 (s, 3H), 2.11 (bm, 5H), 1.91 (bm, 5H), 1.75 (bm, 2H), 1.49 (d, 3H, J=21.6), 1.48 (d, 3H, J=21.6), 1.35 (m, 9H); $^{19}$F NMR (CD$_3$OD) δ −72.9, −129.4; mp 209-211° C., $[α]_D^{20}$+18.7 (c=0.29, MeOH).

Example 2

N-(1-CYANOCYCLOPROPYL)-4-FLUORO-N$^2$-{(1S)-2,2,2-TRIFLUORO-1-[4'-(METHYLSULFONYL)BIPHENYL-4-YL]ETHYL}-L-LEUCINAMIDE

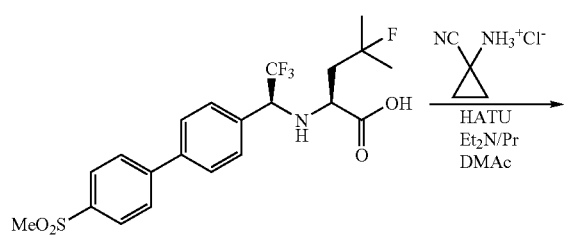

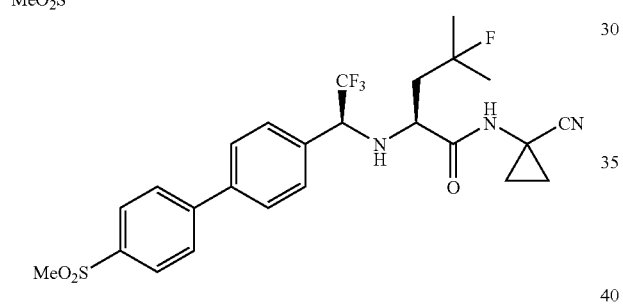

Acid (1.9 g) was dissolved in DMAc (10 mL) and cooled to 0° C. 1-Aminocyclopropane carbonitrile hydrochloride (0.57 g) and HATU (1.85 g) were added. The resulting slurry was stirred for 15 min and DIEA (2.12 mL) was added over 1.5 h. The reaction was aged for 1 h. Water (11.2 mL) was added via dropping funnel over 70 min and the slurry was aged for 1 h at 20° C. The mixture was filtered and the filter cake was washed with a solution of DMAc:water (9.4 mL, 1:1.2), water (18.7 mL), 2-propanol (9.3 mL) The batch was dried to yield 1.67 g, 79% yield of the corresponding amide.

Amide (2.56 g), was dissolved in THF (30.7 mL) at 30° C. Water (19 mL) was added via dropping funnel. The batch was seeded and aged for 1 h at 20° C. Additional water (40.9 mL) was added over 1.5 h and the batch was aged for 16 h. The batch was filtered and washed with water (15 mL). The solids were dried to a constant weight to yield 2.50 g, 97% yield of pure amide. $^1$H NMR (CD$_3$OD) δ 8.17 (bs, 1H), 8.05 (d, 2H, J=8.5), 7.96 (d, 2H, J=8.5), 7.80 (d, 2H, J=8.0), 7.64 (d, 2H, J=8.0), 4.43 (m, 1H), 3.55 (ddd, 1H, J=5.0, 8.5, 8.0), 3.18 (s, 3H), 2.84 (bm, 1H), 2.02 (m, 2H), 1.46 (d, 3H, J=21.5), 1.43 (d, 3H, J=22.0), 1.36 (m, 2H), 1.07 (m, 1H), 0.94 (m, 1H); $^{13}$C NMR (CD$_3$OD) δ; $^{19}$F NMR (CD$_3$OD) δ −73.2, −136.8; IR (cm$^{-1}$) 3331, 2244, 1687, 1304, 1152; mp 223-224° C., $[α]_D^{20}$+23.3 (c=0.53, MeOH).

Example 3

N-(1-CYANOCYCLOPROPYL)-4-FLUORO-N$^2$-[(1S)-2,2,2-TRIFLUORO-1-[4'-(METHYLSULFONYL)BIPHENYL-4-YL]ETHYL}-L-LEUCINAMIDE

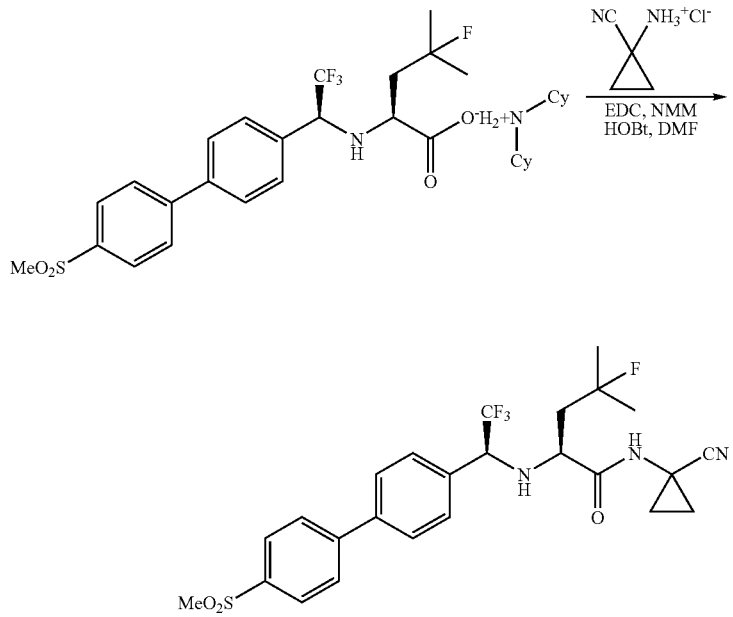

A round-bottom flask was charged with biphenyl acid-.DCHA salt (76.6 g, 99.2% ee, diastereomeric ratio 342:1) and DMF (590 g). Solid aminocyclopropane carbonitrile.HCl (15.2 g), HOBt.H$_2$O (17.9 g), and EDC.HCl (29.1 g) were all charged forming a white slurry. The batch was then heated to 38-42° C. and aged for 5 hours. The batch was then cooled to 20-25° C. and held overnight. HPLC analysis showed 99.4% conversion. The batch was heated to 38-42° C. and water (375 g) was charged to batch over 2 hours. The batch remained as a slurry throughout the water addition. The batch was then heated to 58-62° C. and aged for 1 hour. Following age, water (375 g) was charged over 3 hours, at a rate of 2.1 g/min. The batch was then cooled to 15-25° C. and aged overnight. The batch was filtered and washed with 39% DMF in water (2×300 g) and 2-propanol (180 g). The solids were dried in the filter at 40-60° C. for 24 hours. The desired crude product was isolated as a white solid (57 g, 92% yield, 99.4 wt %). A round-bottom flask was charged with crude solid (57 g) and acetone/water solution (324 g, 88/12). The slurry was then heated to 40° C., at which point the batch was in solution, and aged for an hour. Water (46 g) was then charged over 30 minutes. The batch was then seeded (1.7 g, 3.0 wt %), and the batch was aged at 40° C. for an hour prior to proceeding with the crystallization. Water (255 g) was charged over 4.5 h. The batch was then cooled to 23° C. over 1.5 h, aged for 4 h and filtered. The solids were washed with acetone/water (158 g, 45/55) and water (176 g). The filter cake was dried with nitrogen sweep/vacuum at 55° C. The desired product (57.2 g, 99.9 wt %, 99.8 A % (enantiomer ND), was obtained in 94.9% yield. $^1$H NMR (CD$_3$OD) δ 8.17 (bs, 1H), 8.05 (d, 2H, J=8.5), 7.96 (d, 2H, J=8.5), 7.80 (d, 2H, J=8.0), 7.64 (d, 2H, J=8.0), 4.43 (m, 1H), 3.55 (ddd, 1H, J=5.0, 8.5, 8.0), 3.18 (s, 3H), 2.84 (bm, 1H), 2.02 (m, 2H), 1.46 (d, 3H, J=21.5), 1.43 (d, 3H, J=22.0), 1.36 (m, 2H), 1.07 (m, 1H), 0.94 (m, 1H); $^{13}$C NMR (CD$_3$OD) δ; $^{19}$F NMR (CD$_3$OD) δ −73.2, −136.8; IR (cm$^{-1}$) 3331, 2244, 1687, 1304, 1152; mp 223-224° C., $[\alpha]_D^{20}$+23.3 (c=0.53, MeOH).

What is claimed is:

1. A process for preparing a compound of formula I:

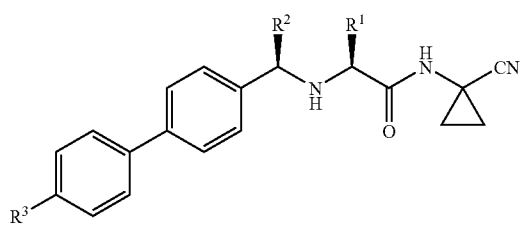

comprising amidating a salt of formula IIA or an acid of formula IIB

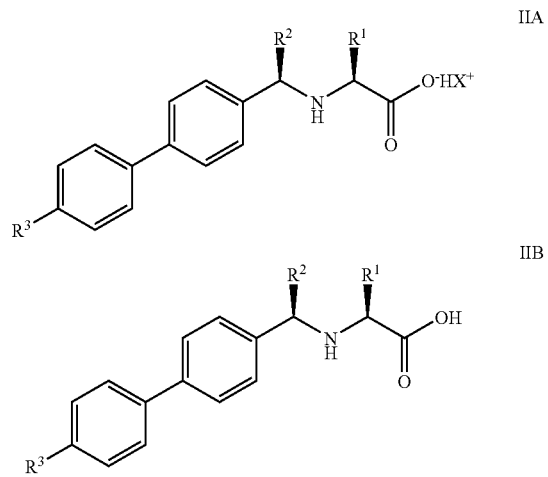

with 1-aminocyclopropane carbonitrile, in the presence of
  a coupling agent, wherein the coupling agent is a carbodiimide, a phosphonium salt or a uronium salt;
  a base, wherein the base is N-methyl morpholine, TEA, N-ethyldiisopropylamine, 2,6-lutidine, 2,4,6 collidine or 1-methylpiperidine;
  a solvent, wherein the solvent is DMF, DMAc, NMP, acetonitrile, THF or DMSO;
  and an activating agent;
  wherein R$^1$ is C$_{1-6}$ alkyl or C$_{1-6}$ haloalkyl;
  R$^2$ is C$_{1-6}$ alkyl or C$_{1-6}$ haloalkyl;
  R$^3$ is SO$_m$(C$_{1-6}$ alkyl);
  X is a tertiary amine, a secondary amine or a metal salt; and
  m is an integer from zero to two.

2. The process of claim 1 wherein the activating agent is N-hydroxy succinimide, 2-hydroxypyridine, N-hydroxyphthalimide, CDI or HOBt.

3. The process of claim 2 wherein the coupling agent is EDC; the activating agent is HOBt; the base is N-methyl morpholine; and the solvent is DMF.

4. The process of claim 1 wherein R$^1$ is C$_{1-6}$ haloalkyl; R$^2$ is C$_{1-6}$ haloalkyl and R$^3$ is SO$_2$(C$_{1-6}$ alkyl).

5. The process of claim 4 wherein R$^1$ is (2-fluoro,2-methyl)propyl; R$^2$ is trifluoromethyl and R$^3$ is SO$_2$CH$_3$.

* * * * *